US012649726B2

(12) United States Patent
Delatour

(10) Patent No.: US 12,649,726 B2
(45) Date of Patent: Jun. 9, 2026

(54) SUBSTITUTED TETRAHYDROISOQUINOLINE DERIVATIVE AS A D1 POSITIVE ALLOSTERIC MODULATOR

(71) Applicant: UCB Biopharma SRL, Brussels (BE)

(72) Inventor: Claude Delatour, Brussels (BE)

(73) Assignee: UCB Biopharma SRL, Brussels (BE)

( * ) Notice: Subject to any disclaimer, the term of this patent is extended or adjusted under 35 U.S.C. 154(b) by 349 days.

(21) Appl. No.: 18/267,331

(22) PCT Filed: Dec. 16, 2021

(86) PCT No.: PCT/EP2021/086066

§ 371 (c)(1),
(2) Date: Jun. 14, 2023

(87) PCT Pub. No.: WO2022/129268

PCT Pub. Date: Jun. 23, 2022

(65) Prior Publication Data

US 2024/0059665 A1 Feb. 22, 2024

(30) Foreign Application Priority Data

Dec. 18, 2020 (EP) .................................... 20215255

(51) Int. Cl.
*C07D 401/06* (2006.01)

(52) U.S. Cl.
CPC .................................. *C07D 401/06* (2013.01)

(58) Field of Classification Search
CPC .................................................... C07D 401/06
See application file for complete search history.

(56) References Cited

U.S. PATENT DOCUMENTS

| | | | | |
|---|---|---|---|---|
| 10,370,355 | B2 * | 8/2019 | Ates | A61P 25/16 |
| 2022/0259179 | A1 | 8/2022 | Ates et al. | |

FOREIGN PATENT DOCUMENTS

| | | |
|---|---|---|
| WO | 2013/066736 | 5/2013 |
| WO | WO2014/193781 | 12/2014 |
| WO | WO 2016/055479 | 4/2016 |
| WO | WO 2017/178377 | 10/2017 |
| WO | 2020/050722 | 3/2020 |
| WO | 2021001288 | 1/2021 |

OTHER PUBLICATIONS

Belles, Pham Biochem and Behavior, vol. 222, 202, 173503, 1-11. (Year: 2023).*
Luderman, Mol Pharmacol, 9:1197-1203, 2018. (Year: 2018).*
Liu, JD Insight, 2023, 8(16), e170434, 1-13. (Year: 2023).*
Lewis, J Pharmacol Exp Ther, 2015, 354:340-349. (Year: 2015).*
International Search Report dated Jan. 21, 2022 for International Application No. PCT/EP2021/086066, 3 pages.
Meanwell (Top Med Chem, 2015, 9:283-382) (Year: 2015).
Hall et al. (J Med Chem, 2018, 62: 128-140) (Year: 2018).
Tian et al., J Pharm Pharmacol, 2010, 62: 1534-1546 (Year: 2010).
Bajpai et al., IUCrJ, 2016, 3:490-439 (Year: 2016).
Kummerer, Klaus "Pharmaceuticals in the environment" Annual review of environment and resources (2010) vol. 35, pp. 57-75.
Wesserling, Martyna et al. "Will in vitro tests replace animal models in experimental oncology?", Journal of tissue science and engineering (2011) vol. 2(1), p. 102e. doi: 10.4172/2157-.
Szajewska, H. "Evidence-based medicine and clinical research: both are needed, neither is perfect", Annals of nutrition and metabolism (2018) vol. 72(3), pp. 13-23.
Brown (Bioisosteres in Medicinal Chemistry, 2012, Ch. 1) (Year: 2012).
Davoren et al. (J Med Chem, 2018, 61 :11384-11387 (Year: 2018).
Girmaw (Health Sci Rep, 2024, 7:e1984) (Year: 2024).
Blanchard et al. (Nat Rev Neural, 2022, 18:25-39) (Year: 2022).
Ke et al. (Aging and Disease, 2021, 12:223-246) (Year: 2021).
Davoren et al. (J Med Chem, 2018, 61 :11384-11397 (Year: 2018) (correction of citation in prior IDS).
Bajpai et al., IUCrJ, 2016, 3:430-439 (Year: 2016) (correction of citation in prior IDS).

* cited by examiner

*Primary Examiner* — D Margaret M Seaman
(74) *Attorney, Agent, or Firm* — McDonnell Boehnen Hulbert & Berghoff LLP

(57) ABSTRACT

The present invention relates to compound according to formula (I) which is a positive allosteric modulator of D1 and accordingly of benefit as pharmaceutical agent for the treatment of diseases in which D1 receptors play a role.

(I)

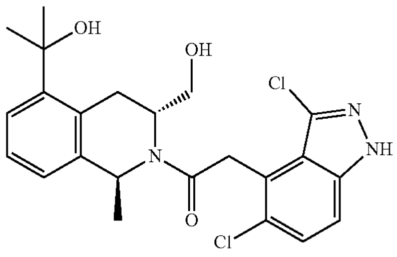

8 Claims, No Drawings

SUBSTITUTED TETRAHYDROISOQUINOLINE DERIVATIVE AS A D1 POSITIVE ALLOSTERIC MODULATOR

CROSS-REFERENCE TO RELATED APPLICATIONS

This application is a U.S. national phase of International Application No. PCT/EP2021/086066, filed Dec. 16 2021, which claims priority from European Patent Application No. 20215255.9, filed Dec. 18, 2020, the disclosure of each of which is hereby incorporated by reference in its entirety.

The invention relates to a tetrahydroisoquinoline derivative and its use in therapy. In particular, the present invention relates to a pharmacologically active substituted tetrahydroisoquinoline derivative.

This compound acts as a D1 Positive Allosteric Modulator and is accordingly of benefit as a pharmaceutical agent for the treatment of diseases in which D1 receptors play a role.

The monoamine dopamine acts via two families of GPCRs to modulate motor function, reward mechanisms, cognitive processes and other physiological functions. Specifically, dopamine is acting upon neurons via D1-like, comprising dopamine D1 and D5, receptors which couple mainly to the Gs G-protein and thereby stimulate cAMP production, and D2-like, which comprise D2, D3 and D4, receptors which couple to Gi/qG-proteins and which attenuate cAMP production. These receptors are widely expressed in different brain regions. In particular, D1 receptors are involved in numerous physiological functions and behavioural processes. D1 receptors are, for instance, involved in synaptic plasticity, cognitive function and goal-directed motor functions, but also in reward processes. Due to their role in several physiological/neurological processes, D1 receptors have been implicated in a variety of disorders including cognitive and negative symptoms in schizophrenia, cognitive impairment related to neuroleptic therapy, Mild Cognitive Impairment (MCI), impulsivity, Attention-Deficit Hyperactivity Disorder (ADHD), Parkinson's disease and other movement disorders, dystonia, Parkinson's dementia, Huntington's disease, dementia with Lewy Body, Alzheimer's disease, drug addiction sleep disorders, apathy, traumatical spinal cord injury or neuropathic pain.

It has proven difficult to develop orally bioavailable small molecules targeting D1 receptors. D1 agonists developed so far are generally characterized by a catechol moiety and their clinical use has therefore been limited to invasive therapies. Achieving sufficient selectivity has also been challenging due to the high degree of homology in the ligand binding site between dopamine receptors subtypes (e.g. dopamine D1 and D5). Also, D1 agonists are associated with potentially limiting side effects including but not limited to dyskinesia and hypotension.

There is therefore a need to design new agents that could modulate D1 receptors.

There has been much interest in the identification of allosteric modulators of GPCRs, both as tools to understand receptor mechanisms and as potential therapeutic agents. GPCRs represent the largest family of cell-surface receptors and a large number of marketed drugs directly activate or block signaling pathways mediated by these receptors. However, for some GPCRs (e.g. peptide receptors), it has proven challenging to develop small molecules or to achieve sufficient selectivity due to the high degree of homology in the ligand binding site between subtypes (e.g. dopamine D1 and D5 or D2 and D3). Accordingly, much drug research has shifted to the identification of small molecules which target sites distinct from the orthosteric natural agonist. Ligands which bind to these sites induce a conformational change in the GPCR thereby allosterically modulating the receptor function. Allosteric ligands have a diverse range of activities including the ability to potentiate (positive allosteric modulator, PAM) or attenuate (negative allosteric modulator, NAM) the effects of the endogenous ligand, by affecting affinity and/or efficacy. As well as subtype selectivity, allosteric modulators may present other potential advantages from a drug discovery perspective such as a lack of direct effect or intrinsic efficacy; only potentiating the effect of the native transmitter where and when it is released; reduced propensity for inducing desensitization arising from constant exposure to an agonist as well as reduced propensity to induce target-related side-effects.

The compound according to the present invention potentiates the effect of D1 agonists or of the endogenous ligand on D1 receptors through an allosteric mechanism and is therefore a D1 Positive Allosteric Modulator (D1 PAM).

The compound in accordance with the present invention, being a D1 PAM, is therefore beneficial in the treatment and/or prevention of diseases and disorders in which D1 receptors play a role. Such diseases include cognitive and negative symptoms in schizophrenia, cognitive impairment related to neuroleptic therapy, Mild cognitive impairment (MCI), impulsivity, Attention-Deficit Hyperactivity Disorder (ADHD), Parkinson's disease and other movement disorders, dystonia, Parkinson's dementia, Huntington's disease, dementia with Lewy Body, Alzheimer's disease, drug addiction, sleep disorders, apathy, traumatic spinal cord injury or neuropathic pain.

International patent application WO 2014/193781 A1 discloses certain 3,4-dihydroisoquinolin-2(1H)-yl derivatives useful for the treatment of cognitive impairment associated with Parkinson's disease or Schizophrenia.

International patent application WO 2017/178377 discloses certain substituted 3,4-dihydroisoquinol-2(1H)-yl derivatives and analogs thereof useful as D1 positive allosteric modulators.

International patent application no PCT/EP2020/068183, published as WO2021/001288, discloses 2-(3,5-dichloro-1-methyl-indazol-4-yl)-1-[(1S,3R)-3-(hydroxymethyl)-5-(1-hydroxy-1-methyl-ethyl)-1-methyl-3,4-dihydro-1H-isoquinolin-2-yl]ethanone.

Nevertheless, there remains a need to develop alternative and potent D1 positive allosteric modulators.

The present invention provides 2-(3,5-dichloro-indazol-4-yl)-1-[(1S,3R)-3-(hydroxymethyl)-5-(1-hydroxy-1-methyl-ethyl)-1-methyl-3,4-dihydro-1H-isoquinolin-2-yl] ethanone of formula (I), (I)

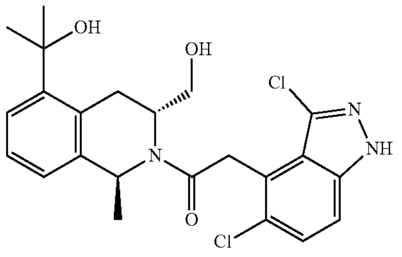

or a pharmaceutically acceptable salt thereof.

The present invention also provides a compound of formula (I) as defined above or a pharmaceutically acceptable salt thereof, for use in therapy.

Although, as stated above, certain D1 PAM compounds have been disclosed in the state of the art, the exact structure of this compound has not previously been disclosed.

In another aspect, the present invention also provides a compound of formula (I) as defined above, or a pharmaceutically acceptable salt thereof, for use in the treatment of diseases and/or disorders in which D1 receptors play a role.

In another aspect, the present invention provides a compound of formula (I) as defined above, or a pharmaceutically acceptable salt thereof, for use in the treatment and/or prevention of cognitive and negative symptoms in schizophrenia, cognitive impairment related to neuroleptic therapy, Mild Cognitive impairment (MCI), impulsivity, Attention-Defficit Hyperactivity Disorder (ADHD), Parkinson's disease and other movement disorders, dystonia, Parkinson's dementia, Huntington's disease, dementia with Lewy Body, Alzheimer's disease drug addiction, sleep disorders, apathy, traumatic spinal cord injury or neuropathic pain.

In a particular embodiment of this aspect, the present invention provides a compound of formula (I) as defined above, or a pharmaceutically acceptable salt thereof for use in the treatment of Parkinson's disease and other movement disorders, Alzheimer's disease, or cognitive and negative symptoms in schizophrenia.

Therefore, in one particular aspect, the present invention provides a compound of formula (I), as defined above, or a pharmaceutically acceptable salt thereof, for use in the treatment of Parkinson's disease and other movement disorders.

In a further aspect, the present invention provides for the use of a compound of formula (I) as defined above, or a pharmaceutically acceptable salt thereof, for the manufacture of a medicament useful for the treatment and/or prevention of diseases and/or disorders in which D1 receptors play a role.

In another further aspect, the present invention provides for the use of a compound of formula (I) as defined above, or a pharmaceutically acceptable salt thereof, for the manufacture of a medicament useful for the treatment and/or prevention of cognitive and negative symptoms in schizophrenia, cognitive impairment related to neuroleptic therapy, Mild Cognitive Impairment (MCI), impulsivity, Attention-Deficit Hyperactivity Disorder (ADHD), Parkinson's disease and other movement disorders, dystonia, Parkinson's dementia, Huntington's disease, dementia with Lewy Body, Alzheimer's disease, drug addiction, sleep disorders, apathy, traumatic spinal cord injury or neuropathic pain.

In a particular embodiment of this aspect, the present invention provides for the use of a compound of formula (I) as defined above, or a pharmaceutically acceptable salt thereof for the manufacture of a medicament useful for the treatment of Parkinson's disease and other movement disorders, Alzheimer's disease, or cognitive and negative symptoms in schizophrenia.

In one particular aspect, the present invention provides for the use of a compound of formula (I), as defined above, or a pharmaceutically acceptable salt thereof, for the manufacture of a medicament useful for the treatment of Parkinson's disease and other movement disorders.

The present invention also provides a method for the treatment and/or prevention of disorders for which the administration of D1 positive allosteric modulator is indicated, which comprises administering to a patient in need of such treatment an effective amount of a compound of formula (I) as defined above, or a pharmaceutically acceptable salt thereof.

In another aspect, the present invention provides a method for the treatment and/or prevention of cognitive and negative symptoms in schizophrenia, cognitive impairment related to neuroleptic therapy, Mild Cognitive Impairment (MCI), impulsivity, Attention-Deficit Hyperactivity Disorder (ADHD), Parkinson's disease and other movement disorders, dystonia, Parkinson's dementia, Huntington's disease, dementia with Lewy Body, Alzheimer's disease, drug addiction, sleep disorders, apathy, traumatic spinal cord injury or neuropathic pain, which comprises administering to a patient in need of such treatment an effective amount of a compound of formula (I) as defined above, or a pharmaceutically acceptable salt thereof.

In a particular embodiment of this aspect, the present invention provides a method for the treatment of Parkinson's disease and other movement disorders, Alzheimer's disease, or cognitive and negative symptoms in schizophrenia, which comprises administering to a patient in need of such treatment of an effective amount of a compound of formula (I) as defined above, or a pharmaceutically acceptable salt thereof.

In one particular aspect, the present invention provides a method for the treatment of Parkinson's disease and other movement disorders, which comprises administering to a patient in need of such treatment of an effective amount of a compound of formula (I) as defined above, or a pharmaceutically acceptable salt thereof.

For use in medicine, the salts of the compound of formula (I) will be pharmaceutically acceptable salts. Other salts may, however, be useful in the preparation of the compound of formula (I) or of its pharmaceutically acceptable salts. Standard principles underlying the selection and preparation of pharmaceutically acceptable salts are described, for example, in *Handbook of Pharmaceutical Salts: Properties, Selection and Use*, ed. P. H. Stahl & C. G. Wermuth, Wiley-VCH, 2002. Suitable pharmaceutically acceptable salts of the compound of formula (I) include acid addition salts which may, for example, be formed by mixing a solution of the compound of formula (I) with a solution of a pharmaceutically acceptable acid.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^{1}H$, $^{2}H$ (deuterium) or $^{3}H$ (tritium) atom, preferably $^{1}H$. Similarly, by way of example, each individual carbon atom present in formula (I), or in the formulae depicted hereinafter, may be present as a $^{12}C$, $^{13}C$, $^{14}C$ atom, preferably $^{12}C$.

The present invention includes within its scope solvates of the compounds of formula (I) above. Such solvates may be formed with common organic solvents or water.

The present invention also includes within its scope co-crystals of the compounds of formula (I) above. The technical term "co-crystal" is used to describe the situation where neutral molecular components are present within a crystalline compound in a definite stoichiometric ratio. The preparation of pharmaceutical co-crystals enables modifications to be made to the crystalline form of an active pharmaceutical ingredient, which in turn can alter its physicochemical properties without compromising its intended biological activity (see *Pharmaceutical Salts and Co-crystals*, ed. J. Wouters & L. Quere, RSC Publishing, 2012).

Compounds according to the present invention may exist in different polymorphic forms. Although not explicitly indicated in the above formula, such forms are intended to be included within the scope of the present invention.

In a particular aspect according to the present invention, the compound of formula (I) is isolated in the form of a monohydrate as further described in the Examples.

The invention also includes within its scope pro-drug forms of the compounds of formula (I) and its various sub-scopes and sub-groups.

Activity in any of the above-mentioned therapeutic indications or disorders can of course be determined by carrying out suitable clinical trials in a manner known to a person skilled in the relevant art for the particular indication and/or in the design of clinical trials in general.

For treating diseases, compound of formula (I) or its pharmaceutically acceptable salts may be employed at an effective daily dosage and administered in the form of a pharmaceutical composition.

Therefore, the present invention also provides a pharmaceutical composition comprising the compound of formula (I) as depicted above, or a pharmaceutically acceptable salt thereof, in association with one or more pharmaceutically acceptable carriers.

To prepare a pharmaceutical composition according to the invention, one or more of the compounds of formula (I) or a pharmaceutically acceptable salt thereof is intimately admixed with a pharmaceutical diluent or carrier according to conventional pharmaceutical compounding techniques known to the skilled practitioner.

Suitable diluents and carriers may take a wide variety of forms depending on the desired route of administration, e.g., oral, rectal, parenteral or intranasal.

Pharmaceutical compositions according to the present invention can, for example, be administered orally, parenterally, i.e., intravenously, intramuscularly or subcutaneously, intrathecally, by inhalation or intranasally.

Pharmaceutical compositions suitable for oral administration can be solids or liquids and can, for example, be in the form of tablets, pills, dragees, gelatin capsules, solutions, syrups, chewing-gums and the like.

To this end the active ingredient may be mixed with an inert diluent or a non-toxic pharmaceutically acceptable carrier such as starch or lactose. Optionally, these pharmaceutical compositions can also contain a binder such as microcrystalline cellulose, gum tragacanth or gelatine, a disintegrant such as alginic acid, a lubricant such as magnesium stearate, a glidant such as colloidal silicon dioxide, a sweetener such as sucrose or saccharin, or colouring agents or a flavouring agent such as peppermint or methyl salicylate.

The invention also contemplates compositions which can release the active substance in a controlled manner. Pharmaceutical compositions which can be used for parenteral administration are in conventional form such as aqueous or oily solutions or suspensions generally contained in ampoules, disposable syringes, glass or plastics vials or infusion containers.

In addition to the active ingredient, these solutions or suspensions can optionally also contain a sterile diluent such as water for injection, a physiological saline solution, oils, polyethylene glycols, glycerine, propylene glycol or other synthetic solvents, antibacterial agents such as benzyl alcohol, antioxidants such as ascorbic acid or sodium bisulphite, chelating agents such as ethylene diamine-tetra-acetic acid, buffers such as acetates, citrates or phosphates and agents for adjusting the osmolarity, such as sodium chloride or dextrose.

These pharmaceutical forms are prepared using methods which are routinely used by pharmacists.

The quantity of a compound of use in the invention required for the prophylaxis or treatment of a particular condition will vary depending on the compound chosen and the condition of the patient to be treated. In general, however, the daily dosage may range from 0.05 to 3000 mg, typically from 0.5 mg to 1000 mg for parenteral compositions.

The compound in accordance with the present invention, or a pharmaceutically acceptable salt thereof may be administered alone (monotherapy) or in combination with L-dopa (combination therapy). Alone or in combination with fractions of the L-dopa doses necessary to ameliorate motor disability in patients, the compounds of formula (I) according to the present invention, or pharmaceutical acceptable salts thereof, may be useful for the treatment of dyskinesia associated with administration of L-dopa. For example, if a compound of formula (I) in accordance with the present invention is used with fractions of the L-dopa doses given to patient or used alone to replace L-dopa, it is believed that compound of formula(I) according to the present invention will be effective against motor disability without inducing troublesome dyskinesia. Therefore it is believed that the compound according to the present invention may be useful for the treatment of motor deficits and levodopa-induced dyskinesia (LID).

Therefore, in one particular aspect, the present invention also provides a compound of formula (I), which is useful for the treatment of levodopa induced dyskinesia (LID).

Compound of formula (I) may be prepared by a two-steps process involving reacting an intermediate of formula (II) with an intermediate of formula (III) wherein P1 and P2 are protecting groups such as tert-butyldimethylsilyl and trimethylsilyl respectively, followed by a deprotection step.

(II)

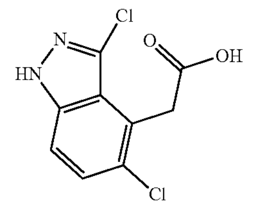

(III)

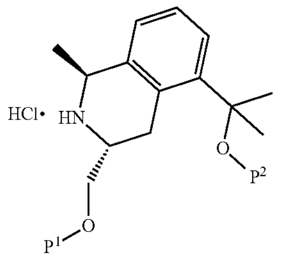

Intermediate (III) may first be conveniently reacted with intermediate of formula (II) in the presence of (1-Cyano-2-ethoxy-2-oxoethylidenaminooxy)dimethylamino-morpholino-carbenium hexafluorophosphate (COMU) or another coupling agent known to the person skilled in the art, in a suitable solvent, e.g. dimethylformamide, with an excess amount of a base, e.g. N,N-diisopropylethylamine.

The resulting intermediate may directly be deprotected using a fluoride-based reagent such as tetrabutyl ammonium fluoride (TBAF) in THF or according to any method known to the person skilled in the art.

Intermediate of formula (III) may be prepared by a process involving reaction of intermediates of formula (IV), (IV)

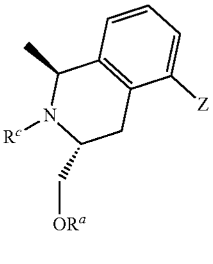

wherein

Z represents halogen or 1-hydroxy-1-methyl ethyl;

$R^a$ represents tert-butyl dimethylsilyl; and $R^c$ represents hydrogen or tert-butoxycarbonyl.

In a first step, intermediate of formula (IV), wherein Z represents bromo, and $R^c$ represents hydrogen, herein after referred to as intermediate (IVa), may be protected with an appropriate protective group, according to methods known to the skilled in the art to afford a compound of formula (IV), wherein Z represents bromo and $R^c$ represents tert-butoxycarbonyl, herein after referred to as intermediate (IVb).

In a second step, a metal-halogen exchange reaction may be performed e.g. in the presence of n-BuLi, in a suitable solvent, e.g. tetrahydrofuran, at low temperature, in the presence of dry acetone under continuous flow, according to a method described in the accompanying Examples, to afford corresponding intermediate (IV) as described above wherein Z represents 1-hydroxy-1-methyl ethyl, herein after referred to as intermediate (IVc).

The tert-butoxycarbonyl (Boc) group ($R^c$) may then first be deprotected according to methods known to the person skilled in the art or as further described in the accompanying Examples to afford intermediate (III).

Intermediate of formula (IVa) may be prepared by a process involving reaction of an intermediate of formula (V), wherein Y is a halogen, e.g. bromo, and $R^a$ is defined above for intermediate of formula (IV).

(V)

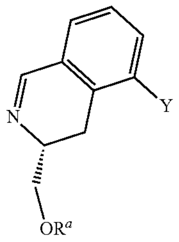

The reaction is conveniently effected in the presence of methyl magnesium chloride, in a suitable solvent e.g. tetrahydrofuran, at low temperature.

Intermediate (V) may be prepared by a 2-step process involving reaction of intermediate of formula (VI), (VI)

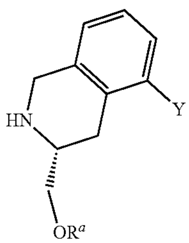

wherein Y is as defined above for intermediate of formula (V) and $R^a$ represents hydrogen or tert-butyl-dimethylsilyl.

In a first step intermediate (VI) wherein $R^a$ represents hydrogen is reacted with tert-butyldimethylsilyl chloride in the presence of a suitable base e.g. 4-dimethylamino-pyridine at room temperature, to afford intermediate (VI) wherein $R^a$ represents tert-butyl-dimethylsilyl.

In a second step, intermediate (VI) wherein $R^a$ represents tert-butyl-dimethylsilyl is reacted with N-Chlorosuccinimide (NCS), in a suitable solvent, e.g. THF to afford intermediate (V).

Intermediate (VI) wherein $R^a$ represents hydrogen may be prepared by a process involving intermediate of formula (VII), wherein Y is as defined above for intermediate (V).

(VII)

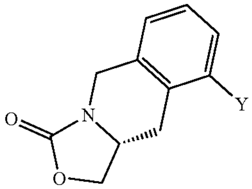

The reaction is conveniently effected in the presence of a strong base, e.g. sodium hydroxide, in a suitable solvent, e.g. mixture of ethanol and water, a high temperature.

Intermediate of formula (VII) may be prepared by a process involving reaction of intermediate (VIII), (VIII)

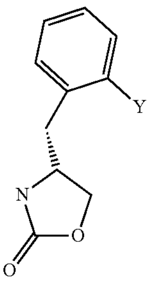

wherein Y is as defined here above for intermediate of formula (V).

The reaction is conveniently effected in the presence of trimethylsilyltriflate and paraformaldehyde, in a suitable solvent e.g. dichloromethane.

Intermediate (VIII) may be prepared by a 2 steps process involving commercially available intermediate (IX), (IX)

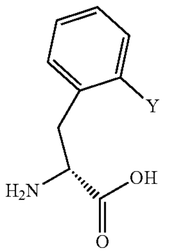

wherein Y is as defined above for intermediate (V).

The reaction is conveniently effected according to the methods described in the accompanying examples or according to methods known to the person skilled in the art.

Intermediate of formula (II) may be prepared by chlorination of an intermediate of formula (X), (X)

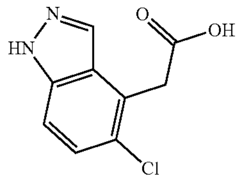

This reaction is conveniently performed using a chlorinating agent such as N-chlorosuccinimide in a polar solvent mixture such DMF at room temperature or according to any method known to the person skilled in the art.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I), this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention. Alternatively the non desired enantiomer may be racemized into the desired enantiomer, in the presence of an acid or a base, according to methods known to the person skilled in the art, or according to methods described in the accompanying Examples.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 3rd edition, 1999. The protecting groups may be removed at any convenient subsequent stage utilising methods known from the art.

The compounds of formula (I) according to the present invention does not directly activate the dopamine D1 receptor, but potentiates the effect of D1 agonists or the endogenous ligand on D1 receptors, dopamine, through an allosteric mechanism, and is therefore D1 positive allosteric modulator (D1 PAM).

Dopamine and other D1 agonists directly activate the dopamine D1 receptor by themselves.

Assays have been designed to measure the effects of compounds in accordance with the present invention in the absence of dopamine ("activation assay") and in the presence of dopamine ("potentiation assay").

The activation assay measures the stimulation of the production of cyclic adenosinemonophosphate (cAMP) in the Homogeneous Time Resolved Fluorescent (HTRF) assay, with the maximum increase in cAMP by increasing concentrations of the endogenous agonist, dopamine, defined as 100% activation.

When tested, compounds of formula (I) according to the present invention lacks significant direct agonist-like effects in that it produces less than 20% of activation (compared to dopamine maximal response) when present in a concentration of 10 μM.

The potentiation assay measures the ability of compounds to increase the levels of cAMP produced by a low-threshold concentration of dopamine. The concentration of dopamine used ([EC20]) is designed to produce 20% stimulation compared to the maximal response (100%) seen with increasing the concentration of dopamine. To measure this potentiation increasing concentrations of the compound with the [EC20] of dopamine are incubated and the potentiation is measured as increases in cAMP production and concentration of compound which produces 50% of the potentiation of the cAMP levels is measured.

When tested in the cAMP HTRF assay, compound of formula (I) according to the present invention has exhibited a value of pEC50 of greater than about 7.5 which shows that it is a D1 Positive Allosteric Modulator.

$GABA_A$ receptor inhibition is known to be intimately linked to seizures and epilepsy. It is therefore desirable to develop compounds which are D1 Positive Allosteric Modulators and which at the same time minimize such effects.

When tested in a GABA-A receptor inhibition assay as described herein, it is therefore desirable that compound of formula (I) displays a percentage of inhibition of the $GABA_A$ receptor of less than about 5%, when measured at a concentration of 10 μM of a compound of formula (I).

cAMP HTRF Assay

The particular conditions in which the compounds have been tested are described here below.

a. Methods D1 Cell Culture

Cells were cultured at 37° C. in a humidified atmosphere of 5% $CO_2$. Cells were grown in DMEM-F12+GlutaMAX™-I medium (GIBCO®, Invitrogen, Merelbeke, Belgium) containing 10% fetal bovine serum (BioWhittaker®, Lonza, Verviers, Belgium), 400 μg/mL Geneticin (GIBCO®), 100 IU/mL Penicillin and 100 IU/mL Streptomycin (Pen-Strep solution, BioWhittaker®). LMtk (Ltk−) mouse fibroblast cells expressing the dopamine D1 receptor (BioSignal Inc, Montreal, Canada, now Perkin Elmer) were used as they have been shown to couple efficiently and give robust functional responses (Watts et al, 1995).

b. cAMP Assay

The measurement of changes in intracellular cyclic adenosinemonophopshpate (cAMP) was determined using the HTRF cAMP dynamic assay kit from CisBio (Codolet, France). Using homogenous time-resolved fluorescence technology, the assay is based on competition between native cAMP produced by cells and cAMP labelled with the dye d2. The tracer binding is determined by an anti-cAMP antibody labeled with cryptate. The effects of the compound alone (agonism) was determined by performing the assay in the absence of dopamine, whilst the effect of the compound as a positive allosteric modulator (PAM) was determined in the presence of an $EC_{20}$ concentration of dopamine. Cells (20,000 per well) are incubated in 384 plates for 1 hour at room temperature in a final volume of 20 μLHBSS (Lonza, with calcium, magnesium and HEPES buffer 20 mM, pH 7.4) containing: isobutyl methylxanthine (Sigma, 0.1 mM final), varying concentrations of test compound (typically $^{9.5}$M to $10^{-4.5}$M) in the presence and absence of dopamine (1.1 nM final). The reaction is then terminated and the cells lysed by adding the d2 detection reagent in lysis buffer (10 microL) and the cryptate reagent in lysis buffer (10 microl) according to manufacturer's instructions. This is then incubated for a further 60 min at room temperature and changes in HTRF fluorescent emission ratio determined according to manufacturer's instructions using an Envision plate reader (Perkin Elmer, Zaventem, Belgium) with laser excitation. All incubations were performed in duplicate and results were compared to a concentration-effect curve to dopamine. ($10^{-11}$M to $10^{-6}$M).

c. Data Analysis

Data was analyzed using Excel and PRISM (GraphPad Software) to obtain $pEC_{50}$ and Erel using the 4-parameter logistic equation (DeLean et al, 1978) where Erel is the fitted maximal response of the test compound minus basal expressed as a percentage relative to that obtained with dopamine which was defined as 100%.

The $pEC_{50}$ of a compound is the −log 10 of the concentration of the compound which produces 50% of the potentiation of the cAMP levels.

The Erel is the relative efficacy, defined as the maximal % potentiation produced by the compound compared to the maximal response produced by increasing concentrations of dopamine (Erel of 1=dopamine maximum response), has been measured.

When tested in the above assay, compound of formula (I) exhibits a value of pEC50 of about 8.2 and an Erel value of about 62%.

Automated Patch Clamp Studies on the $GABA_A$ Receptor Cells

CHO-K1 cells stably expressing human $GABA_A$ receptor α1,β2 and γ2 subunits were used. The cells were harvested using trypsin and maintained in serum-free medium at room temperature. The cells were washed and re-suspended in extracellular solution before testing.

Patch Clamp Studies

Experiments on human $GABA_A$ ($\alpha_1\beta_2\gamma_2$) channels were conducted using an automated patch clamp assay (IonFlux™ HT). Compounds were tested at 3 concentrations (0.1, 1, and 10 μM) in 3 to 4 cells. The external solution for recording $GABA_A$ currents was composed of sodium chloride 137 mM, potassium chloride 4 mM, calcium chloride 1.8 mM, magnesium chloride 1 mM, HEPES 10 mM, and glucose 10 mM. Both external and internal solutions were titrated with NaOH or KOH to obtain a pH of 7.35 or 7.3, respectively. The internal pipette solution contained potassium fluoride 70 mM, potassium chloride 60 mM, sodium chloride 70 mM, HEPES 5 mM, EGTA 5 mM, and Magnesium ATP 4 mM. The final concentration of vehicle used to dilute compounds was 0.33% DMSO in each well. Bicuculline (0.032 to 100 μM) was used as positive control inhibitor. GABA (15 μM) was used as agonist. All recordings were obtained from a holding potential of −60 mV.

The compound addition sequence was the following: one addition of the $EC_{80}$ concentration of GABA was added to establish baseline response. Each concentration of compound was applied for 30 seconds followed by the addition of 15 μM GABA in the presence of the compound for 2 seconds. The process was repeated with the next ascending concentration of compound. Peak inward currents in response to the GABA additions in the presence of a single concentration of compound were measured. All compound data have been normalized to the baseline peak current induced by addition of 15 μM GABA for 2 seconds.

When tested in the above-mentioned assay, at a concentration of 10 μM, compound of represented by formula (I) exhibits a percentage of inhibition of the $GABA_A$ receptor of less than about 0.1% measured at a concentration of 10 μM of a compound of formula (I).

The following Examples illustrates the preparation of compounds of formula (I) according to the present invention.

EXAMPLES

Abbreviations/Recurrent Reagents

ACN: Acetonitrile

Brine: Saturated aqueous sodium chloride solution nBu: n-butyl tBu: tert-butyl

COMU: (1-Cyano-2-ethoxy-2-oxoethylidenaminooxy)dimethylamino-morpholino-carbenium hexafluorophosphate DCM: Dichloromethane DMAP: 4-Dimethylaminopyridine DMF: N,N-Dimethylformamide DMSO: Dimethylsulfoxide $EC_{20/50}$: concentration which produces 20%/50% of the maximum response Erel: relative efficacy $ES^+$: Electrospray Positive Ionisation Et: Ethyl EtOH: Ethanol $Et_2O$: Diethyl ether EtOAc: Ethyl acetate h: Hour HPLC: High Pressure Liquid Chromatography HTRF: homogenous time-resolved fluorescence LCMS: Liquid Chromatography Mass Spectrometry MeOH: Methanol min.: minutes NCS: N-Chlorosuccinimide NMR: Nuclear magnetic resonance iPrOH: isopropanol rt: room temperature SFC: Supercritical Fluid Chromatography TEA: Triethylamine THF: Tetrahydrofuran TLC: Thin Layer Chromatography cAMP: cyclic adenosinemonophosphate IUPAC names have been generated using either Biovia Draw Version 19.1 (2019) or 20.1 (2020)

Analytical Methods

All reactions involving air or moisture-sensitive reagents were performed under a nitrogen or argon atmosphere using dried solvents and glassware. Commercial solvents and reagents were generally used without further purification, including anhydrous solvents when appropriate (generally Sure-Seal™ products from Aldrich Chemical Company or AcroSeal™ from ACROS Organics). In general reactions were followed by thin layer chromatography, HPLC or mass spectrometry analyses.

Mass spectrometric measurements in LCMS mode are performed using different methods and instrument as follows:

Basic LCMS Method 1

A QDA Waters simple quadrupole mass spectrometer is used for LCMS analysis. This spectrometer is equipped with an ESI source and an UPLC Acquity Classic with diode array detector (210 to 400 nm). Data is acquired in a full MS scan from m/z 70 to 800 in positive/negative modes with a basic elution. The reverse phase separation is carried out at 45° C. on a Waters Acquity UPLC BEH C18 1.7 μm (2.1×50 mm) column for basic elution. Gradient elution is done with $H_2O$/ACN/ammonium formate (95/5/63 mg/L)+100 μL/L $NH_4OH$ (solvent A) and ACN/$H_2O$/ammonium formate (95/5/63 mg/L)+100 μL/L $NH_4OH$ (solvent B). Injection volume: 1 μL. Full flow in MS.

| Time (min) | A (%) | B (%) | Flow (mL/min) |
|---|---|---|---|
| 0 | 99 | 1 | 0.8 |
| 0.15 | 99 | 1 | 0.8 |
| 1.6 | 5 | 95 | 0.8 |
| 1.65 | 5 | 95 | 0.8 |
| 2 | 5 | 95 | 0.8 |
| 2.05 | 99 | 1 | 0.8 |
| 2.75 | 99 | 1 | 0.8 |

Acid LCMS Method 1

A QDA Waters simple quadrupole mass spectrometer is used for LCMS analysis. This spectrometer is equipped with an ESI source and an UPLC Acquity with diode array detector (200 to 400 nm). Data is acquired in a full MS scan from m/z 70 to 800 in positive/negative modes with an acidic elution. The reverse phase separation is carried out at 45° C. on a Waters Acquity UPLC HSS T3 1.8 μm (2.1×50 mm) column for acidic elution. Gradient elution is done with $H_2O$/ACN/TFA (95/5/0.05%) (solvent A) and ACN (solvent B).

| Time (min) | A (%) | B (%) | Flow (ml/min) |
|---|---|---|---|
| 0 | 99 | 1 | 0.8 |
| 0.15 | 99 | 1 | 0.8 |
| 1.60 | 5 | 95 | 0.8 |
| 1.65 | 5 | 95 | 0.8 |
| 2 | 5 | 95 | 0.8 |
| 2.05 | 99 | 1 | 0.8 |
| 2.75 | 99 | 1 | 0.8 |

Some reaction mixtures could be treated using Isolute® separator phase cartridges (from Biotage), acidic columns or catch and release SPE (Solid Phase Extraction) cartridges. Crude materials could be purified by normal phase chromatography, preparative TLC, (acidic or basic) reverse phase chromatography, chiral separation, tritiration or recrystallization.

Normal phase chromatography was performed using silica gel columns (100:200 mesh silica gel or cartridges for normal phase column chromatography systems such as Isolera™ Four from Biotage® or Teledyne Isco CombiNormal phase column®).

Products were generally dried under vacuum before final analyses and submission to biological testing.

NMR spectra were recorded on a BRUKER AVANCEIII 400 MHz-Ultrashield NMR Spectrometer fitted with a Windows 7 Professional workstation running Topspin 3.2 software and a 5 mm Double Resonance Broadband Probe (PABBI $^1H/^{19}F$-BB Z-GRD Z82021/0075) or a 1 mm Triple Resonance Probe (PATXI $^1H/D-^{13}C/^{15}N$ Z-GRD Z868301/004).

Chemical shifts are referenced to signals deriving from residual protons of the deuterated solvents (DMSO-$d_6$, MeOH-$d_4$ or $CDCl_3$). Chemical shifts are given in parts per million (ppm) and coupling constants (J) in Hertz (Hz). Spin multiplicities are given as broad (br), singlet (s), doublet (d), triplet (t), quartet (q) and multiplet (m).

All final products were analysed by LCMS in both basic and acid modes, as follows:

Basic LCMS Method 2

A QDA Waters simple quadrupole mass spectrometer is used for LCMS analysis. This spectrometer is equipped with an ESI source and an UPLC Acquity Classic with diode array detector (210 to 400 nm). Data is acquired in a full MS scan from m/z 70 to 800 in positive/negative modes with a basic elution. The reverse phase separation is carried out at 45° C. on a Waters Acquity UPLC BEH C18 1.7 μm (2.1×100 mm) column for basic elution. Gradient elution is done with $H_2O$/ACN/ammonium formate (95/5/63 mg/L)+100 μL/L $NH_4OH$ (solvent A) and ACN/$H_2O$/ammonium formate (95/5/63 mg/L)+100 μL/L $NH_4OH$ (solvent B). Injection volume: 1 μL. Full flow in MS.

| Time (min) | A (%) | B (%) | Flow (mL/min) |
|---|---|---|---|
| 0 | 99 | 1 | 0.4 |
| 0.8 | 99 | 1 | 0.4 |
| 5.30 | 0 | 100 | 0.4 |
| 5.35 | 0 | 100 | 0.5 |
| 7.30 | 0 | 100 | 0.5 |
| 7.35 | 99 | 1 | 0.4 |
| 9 | 90 | 1 | 0.4 |

Acid LCMS Method 2

A QDA Waters simple quadrupole mass spectrometer is used for LCMS analysis. This spectrometer is equipped with an ESI source and an UPLC Acquity Hclass with diode array detector (210 to 400 nm). Data are acquired in a full MS scan from m/z 70 to 800 in positive/negative modes with an acidic elution. The reverse phase separation is carried out at 45° C. on a Waters Acquity UPLC HSS T3 1.8 μm (2.1×100 mm) column for acidic elution. Gradient elution is done with $H_2O$/ACN/TFA (95/5/0.05%) (solvent A) and ACN (solvent B).

| Time (min) | A (%) | B (%) | Flow (mL/min) |
|---|---|---|---|
| 0 | 99 | 1 | 0.4 |
| 0.8 | 99 | 1 | 0.4 |
| 5.3 | 5 | 95 | 0.4 |
| 5.35 | 5 | 95 | 0.5 |
| 7.3 | 5 | 95 | 0.5 |
| 7.35 | 99 | 1 | 0.4 |
| 9 | 99 | 1 | 0.4 |

1. Preparation of Intermediate of Formula (II)-2-(3, 5-dichloro-1H-indazol-4-yl) acetic acid

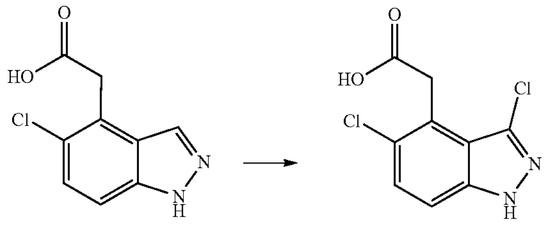

(X) (II)

To a solution of 2-(5-chloro-1H-indazol-4-yl)acetic acid X (CAS: 1904662-08-3, WO2016055479, 2.1 g, 10 mmol) in DMF (10 mL) was added portionwise NCS (1.5 g, 11 mmol) at room temperature and the mixture was stirred overnight. The reaction mixture was quenched by adding 100 mL of water dropwise. The product precipitated after stirring during 1 h. The solid was filtered and washed twice with the mother liquor phase and twice with water (50 mL). The solid was then dried under vacuum at 45° C. overnight to give 2-(3,5-dichloro-1H-indazol-4-yl)acetic acid (2.0 g, 7.62 mmol, 93% purity, 76% yield) which is used in the next step without further purification.

Acid LCMS Method 2 ($ES^+$): 245/247/249 $(M+H)^+$ $^1H$ NMR (400 MHz, DMSO-$d_6$): σ 13.52 (s, 1H), 7.52 (d, J=8.9 Hz, 1H), 7.47 (d, J=8.9 Hz, 1H), 4.21 (s, 2H)

2. Preparation of Compound of Formula (I)

2-(3,5-dichloro-1-methyl-indazol-4-yl)-1-[(1S,3R)-3-(hydroxymethyl)-5-(1-hydroxy-1-methyl-ethyl)-1-methyl-3,4-dihydro-1H-isoquinolin-2-yl]ethanone

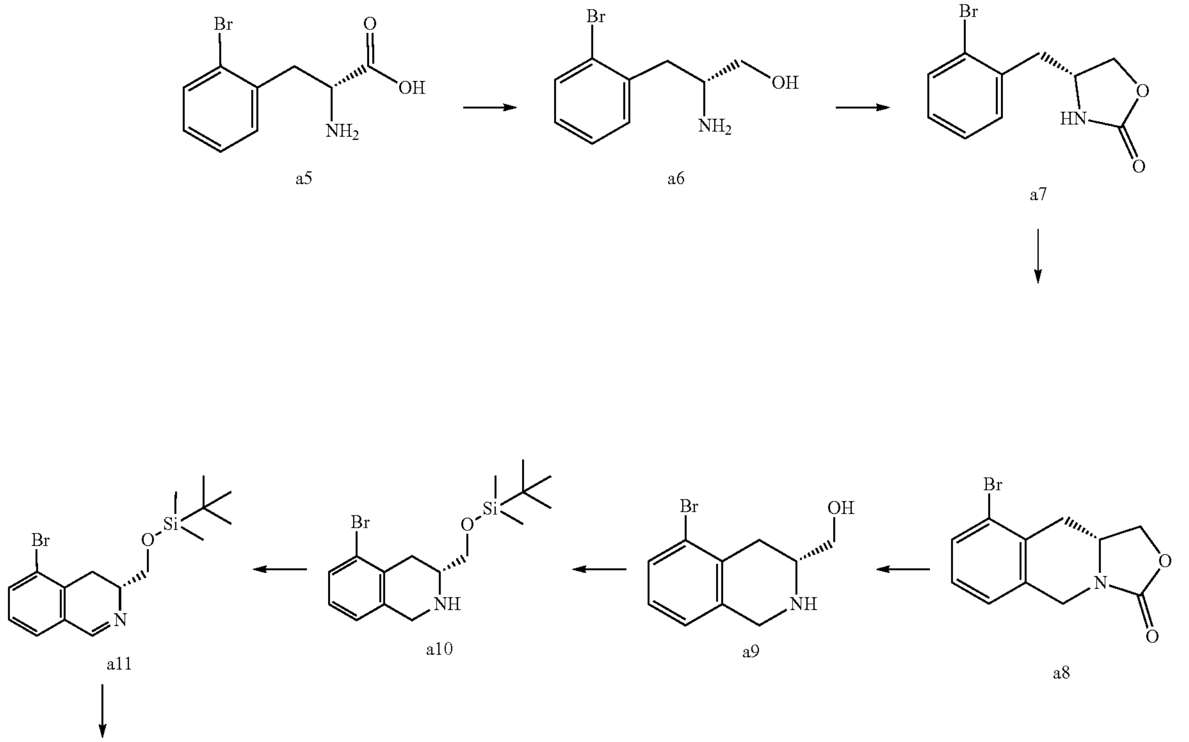

a5 a6 a7 a8 a9 a10 a11

-continued

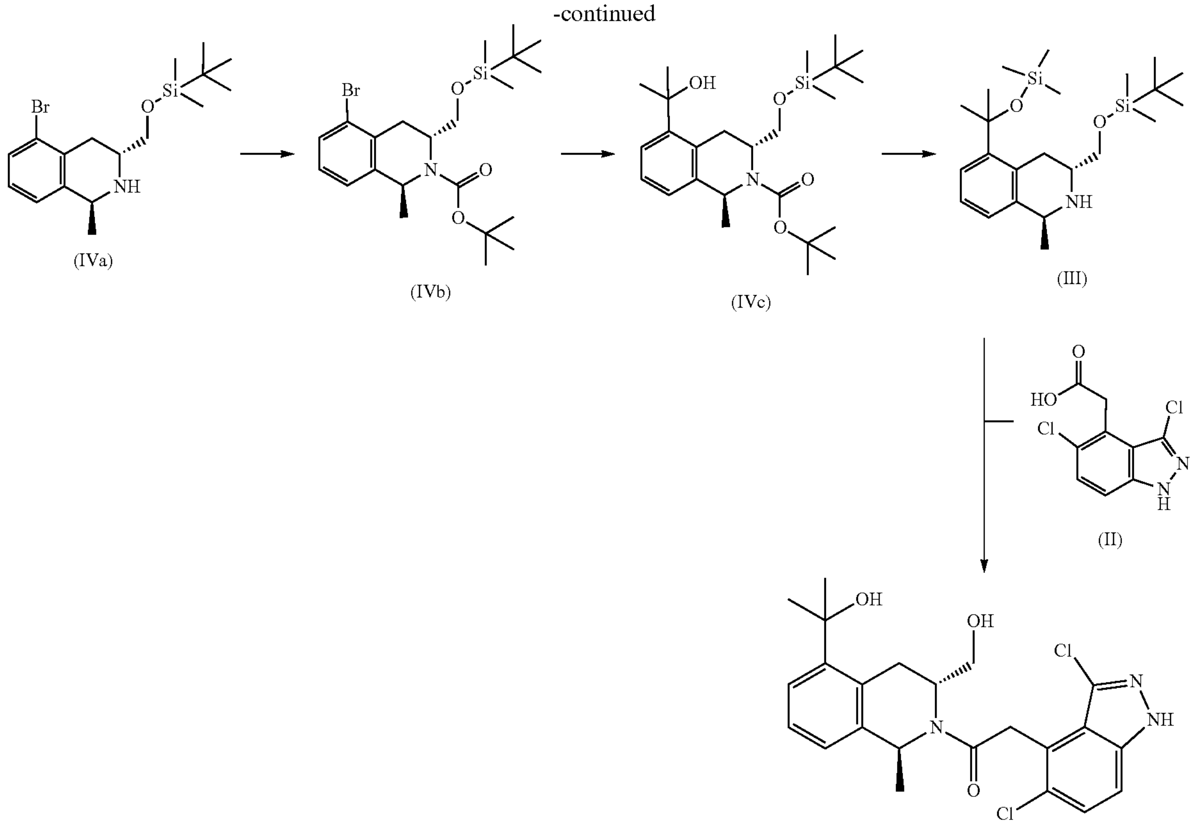

(IVa) (IVb) (IVc) (III) (II) (I)

2.1. Preparation of Intermediate (IX) (2R)-2-amino-3-(2-bromophenyl)propan-1-ol-a6

(2R)-2-amino-3-(2-bromophenyl)propanoic acid a5 (34.0 kg, 139 mol) and THF (238 L) are charged into a reactor. Sodium borohydride (15.6 kg, 413 mol) is added slowly at 20-30° C. A solution of iodine (35.3 kg, 139 mol) in dry THF (20.0 L) is added slowly at 0-10° C. and the reaction mixture is stirred at 70° C. for 12 h. The reaction was quenched with methanol (70.0 L) at 0° C. and heated to 80° C. for 30 min. The mixture was cooled down, concentrated under vacuum and the residue was suspended in NaOH (30.0 L, 2N), then filtered. The filter cake was dried under vacuum to give (2R)-2-amino-3-(2-bromophenyl)propan-1-ol a6 as a white solid (31.0 kg, 135 mol, 96.7% yield) which is used in the next step without further purification. $^{1}$H NMR (400 MHz, $CDCl_3$) σ 7.57 (d, J=7.7 Hz, 1H), 7.21-7.29 (m, 2H), 7.07-7.15 (m, 1H), 3.66 (dd, J=10.5, 3.6 Hz, 1H), 3.41 (dd, J=10.5, 7.2 Hz, 1H), 3.18-3.29 (m, 1H), 2.95 (dd, J=13.5, 5.5 Hz, 1H), 2.70 (dd, J=13.5, 8.2 Hz, 1H), 1.51-1.91 (m, 3H).

2.2. Preparation of Intermediate of Formula (VIII) (4R)-4-[(2-bromophenyl)methyl]oxazolidin-2-one-a7

(2R)-2-amino-3-(2-bromophenyl)propan-1-ol a6 (31.0 kg, 135 mol) and dichloromethane (220 L) are charged into a reactor. Triphosgene (13.9 kg, 47.1 mol) is added at room temperature then N,N-diisopropylethylamine (39.1 kg, 303 mol) is slowly added at 0-10° C. The reaction mixture is stirred at 0-10° C. for 1 h then washed with water (50.0 L) twice, dried with anhydrous sodium sulfate and filtered to give (4R)-4-[(2-bromophenyl)methyl]oxazolidin-2-one a7 as a solution in dichloromethane which is used directly in the next step.

2.3. Preparation of Intermediate (VII) (10aR)-9-bromo-1,5,10,10a-tetrahydrooxazolo[3,4-b]isoquinolin-3-one a8

A solution of (4R)-4-[(2-bromophenyl)methyl]oxazolidin-2-one a7 (135 mol) in dichloromethane (220 L) is charged into a reactor and cooled down to 0-5° C. Trimethylsilyl triflate (35.9 kg, 162 mol) and paraformaldehyde (13.3 kg, 148 mol) are added at 0-5° C., then stirred for 2 h at 15-20° C. Water (170 L) is added into the mixture which is then extracted twice with dichloromethane (50.0 L). the organic layer is dried with anhydrous sodium sulfate, filtered and concentrated under vacuum. A mixture of petroleum ether:ethyl acetate (1:1, 45.0 L) is added and the mixture is stirred at room temperature for 6 h and filtered. The solid was dried to get (10aR)-9-bromo-1,5,10,10a-tetrahydrooxazolo[3,4-b]isoquinolin-3-one a8 as an off-white solid (29.0 kg, 80.2% yield).

$^{1}$H NMR (400 MHz, $CDCl_3$) σ 7.45-7.52 (m, 1H), 7.08-7.14 (m, 2H), 4.83 (d, J=17.0 Hz, 1H), 4.62 (t, J=8.4 Hz, 1H), 4.36 (d, J=17.0 Hz, 1H), 4.21 (dd, J=8.6, 4.9 Hz, 1H), 3.91-3.99 (m, 1H), 3.25 (dd, J=16.3, 4.2 Hz, 1H), 2.67 (dd, J=16.1, 11.0 Hz, 1H).

2.4. Preparation of Intermediates (VI) 2.4.1. [(3R)-5-bromo-1,2,3,4-tetrahydroisoquinolin-3-yl]methanol a9

Ethanol (120 L) and water (60.0 L) are mixed into a reactor. (10aR)-9-bromo-1,5,10,10a-tetrahydrooxazolo[3,4- b]isoquinolin-3-one a8 (29.7 kg, 111 mol) is added then sodium hydroxide (13.3 kg, 332 mol) is slowly added at 15-20° C. The reaction mixture is stirred at 90° C. for 2 h then cooled down to room temperature. Water (300 L) is added into the mixture which is centrifugated. The centrifugal cake is dried in circulation oven to give [(3R)-5-bromo-1,2,3,4-tetrahydroisoquinolin-3-yl]methanol a9 as a white solid (23.7 kg, 88.3% yield) which is used in the next step without further purification.

$^1$H NMR (400 MHz, $CDCl_3$) σ 7.37-7.47 (m, 1H), 6.95-7.08 (m, 2H), 4.00-4.10 (m, 2H), 3.85 (dd, J=10.9, 3.7 Hz, 1H), 3.57 (dd, J=10.9, 7.9 Hz, 1H), 3.06 (ddt, J=11.3, 7.6, 4.1, 4.1 Hz, 1H), 2.79 (dd, J=17.1, 4.4 Hz, 1H), 2.40 (dd, J=17.1, 10.9 Hz, 1H), 1.93 (br s, 2H).

2.4.2. [(3R)-5-bromo-1,2,3,4-tetrahydroisoquinolin-3-yl]methoxy-tert-butyl-dimethyl-silane a10

[(3R)-5-bromo-1,2,3,4-tetrahydroisoquinolin-3-yl] methanol a9 (23.7 kg, 97.8 mol) and dichloromethane (240 L) are charged into a reactor. DMAP (120 g, 0.98 mol) and imidazole (13.3 kg, 196 mol) are added. Tert-butyldimethylsilyl chloride (TBSCl) (17.7 kg, 117 mol) is slowly added at 15-20° C. and the mixture is stirred for 12 h. Ammonium chloride (100 L) is added into the mixture. The organic phase was separated, washed with water (50.0 L), dried with anhydrous sodium sulfate, filtered and concentrated under vacuum to give [(3R)-5-bromo-1,2,3,4-tetrahydroisoquinolin-3-yl]methoxy-tert-butyl-dimethyl-silane a10 as a yellow oil (37.6 kg, 86% purity, 93% yield) which is used in the next step without further purification. $^1$H NMR (400 MHz, $CDCl_3$) σ 7.36-7.45 (m, 1H), 7.01 (d, J=4.6 Hz, 1H), 4.01-4.13 (m, 2H), 3.84 (dd, J=9.9, 3.7 Hz, 1H), 3.64 (dd, J=9.8, 7.2 Hz, 1H), 2.96-3.08 (m, 1H), 2.75 (dd, J=17.0, 4.2 Hz, 1H), 2.44 (dd, J=17.0, 10.8 Hz, 1H), 1.76-2.20 (m, 2H), 0.89-0.97 (m, 9H), 0.08-0.14 (m, 6H).

2.5. Preparation of Intermediate (V) [(3R)-5-bromo-3,4-dihydroisoquinolin-3-yl]methoxy-tert-butyl-dimethyl-silane a11

[(3R)-5-bromo-1,2,3,4-tetrahydroisoquinolin-3-yl] methoxy-tert-butyl-dimethyl-silane a10 (3.42 kg, 8.31 mol) and THF (30.0 L) are charged into a reactor. N-Chlorosuccinimide (NCS) (1.17 kg, 8.73 mol) is slowly added at room temperature and the mixture is stirred at 25° C. for 30 min. A solution of KOH (1.52 kg, 27.1 mol) in dry methanol (7.00 L) is slowly added at room temperature and the reaction is stirred at 25° C. for 1 h. The reaction is quenched with water (10.0 L) and extracted with petroleum ether:ethyl acetate (1:2, 5.00 L). The organic layer is separated, washed with brine (10.0 L), dried with anhydrous sodium sulfate and filtered. This overall procedure is carried out on 10 batches of the same size in parallel and the 10 reaction filtrates are combined and concentrated under vacuum to give [(3R)-5-bromo-3,4-dihydroisoquinolin-3-yl]methoxy-tert-butyl-dimethyl-silane a11 as a brown oil (28.0 kg, crude) which is used in the next step without further purification. $^1$H NMR (400 MHz, $CDCl_3$) σ 8.24 (d, J=2.6 Hz, 1H), 7.58 (dd, J=7.8, 1.2 Hz, 1H), 7.12-7.25 (m, 2H), 4.03 (dd, J=9.5, 4.0 Hz, 1H), 3.67-3.77 (m, 2H), 3.07 (dd, J=17.0, 6.2 Hz, 1H), 2.68 (dd, J=17.1, 10.9 Hz, 1H), 0.88-0.91 (m, 9H), 0.07 (d, J=1.5 Hz, 6H).

2.6. Preparation of Intermediates of Formula (IV)

2.6.1. [(1S,3R)-5-bromo-1-methyl-1,2,3,4-tetrahydroisoquinolin-3-yl]methoxy-tert-butyl-dimethyl-silane (IVa)

[(3R)-5-bromo-3,4-dihydroisoquinolin-3-yl]methoxy-tert-butyl-dimethyl-silane a11 (3.10 kg, 8.75 mol) and THF (20.0 L) are charged into a reactor. The mixture is cooled down to 0° C. and methylmagnesium chloride (3M, 11.6 L) is added. The mixture is stirred at 20° C. for 12 h. The reaction is quenched with a saturated solution of ammonium chloride. The phases are separated and the aqueous layer is extracted twice with petroleum ether:ethyl acetate (3:1, 5.00 L). The combined organic phases are washed with brine (10.0 L), dried over anhydrous sodium sulfate and filtered. This overall procedure is carried out on 9 batches of the same size in parallel and the nine reaction filtrates are combined and concentrated under vacuum. The crude mixture is purified by silica gel chromatography with petroleum ether:ethyl acetate (10:1) to give [(1S,3R)-5-bromo-1-methyl-1,2,3,4-tetrahydroisoquinolin-3-yl]methoxy-tert-butyl-dimethyl-silane (IVa) as a brown oil (4.60 kg, 99.7% purity, 15.7% yield).

$^1$H NMR (400 MHz, DMSO-$d_6$) σ 7.41 (dd, J=7.7, 0.9 Hz, 1H), 7.12-7.18 (m, 1H), 7.03-7.11 (m, 1H), 4.12 (q, J=6.8 Hz, 1H), 3.62 (d, J=5.7 Hz, 2H), 3.07-3.17 (m, 1H), 2.67-2.76 (m, 1H), 2.26 (dd, J=16.9, 10.0 Hz, 1H), 2.12 (br s, 1H), 1.32 (d, J=6.8 Hz, 3H), 0.84-0.93 (m, 9H), 0.07 (d, J=0.9 Hz, 6H).

2.6.2. tert-butyl (1S,3R)-5-bromo-3[[tert-butyl(dimethyl)silyl]oxymethyl]-1-methyl-3,4-dihydro-1H-isoquinoline-2-carboxylate (IVb)

[(1S,3R)-5-bromo-1-methyl-1,2,3,4-tetrahydroisoquinolin-3-yl]methoxy-tert-butyl-dimethyl-silane (IVa) (1.85 kg, 4.99 mol) and dichloromethane (13.0 L) are charged in a reactor. N,N-diisopropylethylamine (1.94 kg, 14.9 mol) and di-tert-butyl dicarbonate (1.14 kg, 5.24 mol) are added at room temperature and the mixture is stirred for 12 h. The reaction mixture is washed twice with a saturated ammonium chloride solution (10.0 L), the organic layer is dried with anhydrous sodium sulfate and filtered. This overall procedure is carried out on 2 batches of the same size in parallel and the two reaction filtrates are combined and concentrated under vacuum. The crude mixture is purified by silica gel chromatography with petroleum ether:ethyl acetate (30:1) to give tert-butyl (1S,3R)-5-bromo-3-[[tert-butyl(dimethyl)silyl]oxymethyl]-1-methyl-3,4-dihydro-1H-isoquinoline-2-carboxylate (IVb) as a yellow oil (4.00 kg, 99.5% purity, 85.2% yield).

$^1$H NMR (400 MHz, DMSO-$d_6$) σ 7.50 (d, J=7.9 Hz, 1H), 7.22 (br d, J=6.7 Hz, 1H), 7.06-7.18 (m, 1H), 4.84 (br s, 1H), 4.12 (br s, 1H), 3.46 (br d, J=15.4 Hz, 2H), 2.94 (br dd, J=15.8, 5.2 Hz, 1H), 2.71 (br t, J=9.5 Hz, 1H), 1.45 (s, 9H), 1.28 (br s, 3H), 0.81 (s, 9H), −0.08 (s, 6H).

2.6.3. tert-butyl (1S,3R)-3[[tert-butyl(dimethyl)silyl]oxymethyl]-5-(1-hydroxy-1-methyl-ethyl)-1-methyl-3,4-dihydro-1H-isoquinoline-2-carboxylate (IVc)

A solution of tert-butyl (1S,3R)-5-bromo-3[[tert-butyl(dimethyl)silyl]oxymethyl]-1-methyl-3,4-dihydro-1H-isoquinoline-2-carboxylate (IVb) (42.5 g, 90.3 mmol) in dry THF (0.5 M solution) and a commercial solution of n-Buthylithium in Hexanes (1.6 M solution) were pumped at respectively 6.0 ml/min (1.0 equiv) and 2.46 mL/min (1.3 equiv.) and were mixed in a glass microchip cooled at −40° C. The mixed flow stream was pumped through the reaction zone 1 of the microchip (0.3 mL) and was then combined with a solution of dry acetone (13.5 M) pumped at 6.0 mL/min (27 equiv.). The resulting stream was then passed through the reaction zone 2 of the microchip (0.7 mL) at −40° C. Finally, the global flow stream exiting the reactor was collected and quenched at room temperature in a saturated solution of aqueous ammonium chloride. When all the feed solutions were consumed, a bilayer reaction mixture was obtained. The aqueous layer was separated from the organic layer, and then extracted twice with ethyl acetate. The combined organic layers were washed with brine, dried over anhydrous sodium sulfate and concentrated under vacuum. A yellow oil was obtained (46.5 g) and was purified by SFC chromatography on a GreenSep Nitro column (10μ, 5×22.3 using $CO_2$ 98%/EtOH 2% eluent). The solvent was removed under vacuum to yield to a white solid, tert-butyl (1S,3R)-3[[tert-butyl(dimethyl)silyl]oxymethyl]-5-(1-hydroxy-1-methyl-ethyl)-1-methyl-3,4-dihydro-1H-isoquinoline-2-carboxylate (IVc) (25 g, 56 mmol, 62% yield).

UPLC_MS basic: 1 peak @ 3.83 min (ES+): 350 $(M-Boc+H)^+$, 332 $(M-Boc-H_2O+H)^+$, 100% purity.

$^1H$ NMR (400 MHz, DMSO-$d_6$) σ 7.44 (d, J=7.9 Hz, 1H), 7.19 (dt, J=8.1, 5.2 Hz, 1H), 7.09 (t, J=9.0 Hz, 1H), 4.99 (s, 1H), 4.87 (dq, J=13.4, 6.4 Hz, 1H), 4.11 (s, 1H), 3.96 (t, J=14.9 Hz, 1H), 3.48 (dd, J=9.4, 4.1 Hz, 1H), 2.98 (dd, J=16.5, 5.0 Hz, 1H), 2.89 (t, J=9.6 Hz, 1H), 1.65 (s, 3H), 1.58 (s, 3H), 1.55 (d, J=2.5 Hz, 9H), 1.34 (dd, J=20.5, 6.6 Hz, 3H), 0.90 (s, 9H), 0.08 (d, J=7.2 Hz, 3H), −0.00 (s, 3H).

2.7. Preparation of Intermediate (III) tert-butyl-dimethyl-[[(1S,3R)-1-methyl-5-(1-methyl-1-trimethylsilyloxy-ethyl)-1,2,3,4-tetrahydroisoquinolin-3-yl]methoxy]silane Tert-butyl(1S,3R)-3[[tert-butyl(dimethyl)silyl]oxymethyl]-5-(1-hydroxy-1-methyl-ethyl)-1-methyl-3,4-dihydro-1H-isoquinoline-2-carboxylate (IVc) (148 g, 87% purity, 287 mmol) is dissolved in 1000 mL dichloromethane and transferred to a 2 liter double walled reactor. 2,6-Lutidine (100 mL, 860 mmol) is added and the jacket temperature is set at −2° C. Trimethylsilyl trifluoromethanesulfonate (154 g, 129 mL, 692 mmol) is added over 40 min via an addition funnel. Two hours after the start of addition, the reaction is quenched by adding 650 mL of an aqueous citric acid solution (1M) and the temperature of the mixture is brought back to 20° C. One hour after the start of the quench, the layers are separated. The organic layer is washed twice with 350 mL of an aqueous solution of citric acid (1M). The organic layer is stirred with 750 mL of aqueous sodium carbonate (10% w/w) for 10 min before separation of the layers. The organic layer is dried over anhydrous sodium sulfate. The organic layer is then filtered and the filtrate is concentrated under vacuum at 40° C. providing a yellow oil (128 g) of tert-butyl-dimethyl-[[(1S,3R)-1-methyl-5-(1-methyl-1-trimethylsilyloxy-ethyl)-1,2,3,4-tetrahydroisoquinolin-3-yl]methoxy]silane (III) which is used in the next step without further purification.

$^1H$ NMR (400 MHz, $CDCl_3$) σ 7.19 (d, J=7.7 Hz, 1H), 7.07 (t, J=7.7 Hz, 1H), 7.00 (d, J=7.6 Hz, 1H), 4.24 (q, J=6.8 Hz, 1H), 3.75 (dd, J=9.7, 4.4 Hz, 1H), 3.60 (dd, J=9.7, 7.0 Hz, 1H), 3.54 (dd, J=16.3, 3.5 Hz, 1H), 3.15 (ddt, J=10.9, 7.4, 4.0 Hz, 1H), 2.52 (dd, J=16.3, 10.9 Hz, 1H), 1.66 (d, J=14.6 Hz, 6H), 1.52-1.43 (m, 3H), 0.92 (q, J=1.2 Hz, 9H), 0.14 (q, J=1.2 Hz, 2H), 0.09 (d, J=1.1 Hz, 6H), 0.00 (q, J=1.2, 0.8 Hz, 9H).

2.8. Preparation of Compound of Formula (I) 2-(3,5-dichloro-1H-indazol-4-yl)-1-[(1S,3R)-3-(hydroxymethyl)-5-(1-hydroxy-1-methyl-ethyl)-1-methyl-3,4-dihydro-1H-isoquinolin-2-yl]ethanone To a solution of 2-(3,5-dichloro-1H-indazol-4-yl)acetic acid (II) (200 mg, 0.82 mmol) in DMF (2.00 mL) at rt were added tert-butyl-dimethyl-[[(1S,3R)-1-methyl-5-(1-methyl-1-trimethylsilyloxy-ethyl)-1,2,3,4-tetrahydroisoquinolin-3-yl]methoxy]silane (413 mg, 0.98 mmol), DIPEA (405 μL, 2.44 mmol) and COMU (398 mg, 0.90 mmol). The resulting reaction mixture was stirred at rt for 1 h. The reaction mixture was diluted with EtOAc and water, the layers were separated and the aqueous layer was extracted with EtOAc (3×). The combined organic layers were washed with water (3×), a saturated $NaHCO_3$ aqueous solution, brine, dried over $Na_2SO_4$, filtered and concentrated to give a brown residue. The crude was filtered through silica (25 g SFAR silica gel column in a gradient of Heptane:EtOAc 100:0 to 0:100) to give a (1:1) mixture of 1-[(1S,3R)-3[[tert-butyl(dimethyl)silyl]oxymethyl]-1-methyl-5-(1-methyl-1-trimethylsilyloxy-ethyl)-3,4-dihydro-1H-isoquinolin-2-yl]-2-(3,5-dichloro-1H-indazol-4-yl)ethanone and 1-[(1S,3R)-3[[tert-butyl(dimethyl)silyl]oxymethyl]-5-(1-hydroxy-1-methyl-ethyl)-1-methyl-3,4-dihydro-1H-isoquinolin-2-yl]-2-(3,5-dichloro-1H-indazol-4-yl)ethanone as a yellow oil (320 mg) which was directly dissolved in THF (3 mL) at rt before addition of TBAF (1.02 mL, 1.02 mmol). The resulting reaction mixture was stirred at room temperature for 1 h. The reaction mixture was diluted with EtOAc and water, the layers were separated and the organic layer was washed with water (3×), dried over $N_2SO_4$, filtered and concentrated to give a colorless oil. The crude was purified by reverse phase flash chromatography Biotage Isolera Four in basic conditions (by portions of 1.0 g, C18 SNAP 60 g gel column in a gradient from 20% to 100% $CH_3CN$ in Water/$NH_4OH$) to afford 2-(3,5-dichloro-1H-indazol-4-yl)-1-[(1S,3R)-3-(hydroxymethyl)-5-(1-hydroxy-1-methyl-ethyl)-1-methyl-3,4-dihydro-1H-isoquinolin-2-yl]ethanone (I) (37.0 mg, 0.08 mmol, 10% yield) as a white solid. Basic LCMS Method 2: 1 peak @ 3.72 min $(ES^+)$: 462 $[M+H]^+$, 98% purity. Acid LCMS Method 2: 1 peak @ 4.14 min $(ES^+)$: 462 $[M+H]^+$, 98% purity.

$^1H$ NMR (400 MHz, DMSO-$d_6$) σ 7.54-7.49 (m, 1H), 7.49-7.43 (m, 1H), 7.40 (dd, J=7.5, 1.8 Hz, 0.3H), 7.35 (dd, J=7.9, 1.3 Hz, 0.7H), 7.23-7.04 (m, 2H), 5.31 (q, J=6.6 Hz, 0.3H), 5.14 (s, 0.3H), 5.12 (s, 0.7H), 5.05 (q, J=6.4 Hz, 0.7H), 4.96 (t, J=5.5 Hz, 0.7H), 4.64-4.30 (m, 3H), 4.17 (q, J=5.4 Hz, 0.3H), 4.10-3.98 (m, 1H), 3.30 (tt, J=9.8, 5.0 Hz, 1H), 3.05 (dd, J=16.1, 4.4 Hz, 1H), 2.97 (p, J=7.8, 6.3 Hz, 1H), 1.57 (d, J=9.6 Hz, 6H), 1.53 (s, 1H), 1.24 (d, J=6.5 Hz, 2H).

The invention claimed is:

1. A compound of formula (I), or a pharmaceutically acceptable salt thereof, (I)

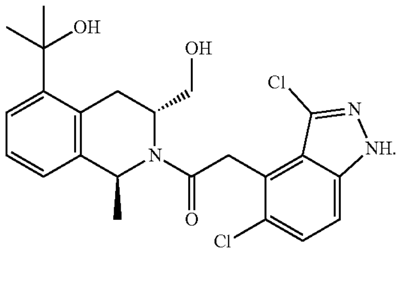

2. A method for the treatment of disorders for which the administration of D1 positive allosteric modulator is indicated, which comprises administering to a patient in need of such treatment an effective amount of a compound of formula (I) according to claim 1, or a pharmaceutically acceptable salt thereof.

3. A method for the treatment of cognitive and negative symptoms in schizophrenia, cognitive impairment related to neuroleptic therapy, Mild Cognitive Impairment (MCI), impulsivity, Attention-Deficit Hyperactivity Disorder (ADHD), Parkinson's disease and other movement disorders, dystonia, Parkinson's dementia, Huntington's disease, dementia with Lewy Body, Alzheimer's disease, drug addiction, sleep disorders, apathy, traumatic spinal cord injury or neuropathic pain, which comprises administering to a patient in need of such treatment an effective amount of a compound of formula (I) according to claim 1, or a pharmaceutically acceptable salt thereof.

4. A pharmaceutical composition comprising a compound of formula (I) as defined in claim 1, or a pharmaceutically acceptable salt thereof, in association with a pharmaceutically acceptable carrier.

5. A compound which is 2-(3,5-dichloro-indazol-4-yl)-1-[(1S,3R)-3-(hydroxymethyl)-5-(1-hydroxy-1-methyl-ethyl)-1-methyl-3,4-dihydro-1H-isoquinolin-2-yl]ethanone or a pharmaceutically acceptable salt thereof.

6. A method for the treatment of disorders for which the administration of D1 positive allosteric modulator is indicated, which comprises administering to a patient in need of such treatment an effective amount of a compound according to claim 5 or a pharmaceutically acceptable salt thereof.

7. A method for the treatment of cognitive and negative symptoms in schizophrenia, cognitive impairment related to neuroleptic therapy, Mild Cognitive Impairment (MCI), impulsivity, Attention-Deficit Hyperactivity Disorder (ADHD), Parkinson's disease and other movement disorders, dystonia, Parkinson's dementia, Huntington's disease, dementia with Lewy Body, Alzheimer's disease, drug addiction, sleep disorders, apathy, traumatic spinal cord injury or neuropathic pain, which comprises administering to a patient in need of such treatment an effective amount of a compound according to claim 5 or a pharmaceutically acceptable salt thereof.

8. A pharmaceutical composition comprising a compound according to claim 5 or a pharmaceutically acceptable salt thereof in association with a pharmaceutically acceptable carrier.

* * * * *